(12) United States Patent
Amanullah et al.

(10) Patent No.: US 8,322,226 B2
(45) Date of Patent: Dec. 4, 2012

(54) METHOD AND APPARATUS FOR QUALITY CONTROL AND QUALITY ASSURANCE OF SIZED BRIDGING MATERIALS USED IN DRILL-IN FLUID FORMULATION

(75) Inventors: Md. Amanullah, Dhahran (SA);
Abdulaziz S. Bubshait, Dammam (SA);
Darrell W. Foreman, Dhahran (SA);
Clayton L. Miller, Denver, CO (US);
John T. Allen, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 294 days.

(21) Appl. No.: 12/897,910

(22) Filed: Oct. 5, 2010

(65) Prior Publication Data
US 2012/0079888 A1    Apr. 5, 2012

(51) Int. Cl.
*G01N 3/08*  (2006.01)
(52) U.S. Cl. .......................................................... 73/821
(58) Field of Classification Search ................... 73/821, 73/818, 866, 7, 856
See application file for complete search history.

(56) References Cited

U.S. PATENT DOCUMENTS

| | | | |
|---|---|---|---|
| 3,318,538 A | 5/1967 | Needham | |
| 3,465,972 A | 9/1969 | Ardary et al. | |
| 4,581,253 A | 4/1986 | Evans et al. | |
| 4,633,712 A | 1/1987 | Scieszka | |
| 4,677,843 A | 7/1987 | Schroeder | |
| 5,029,760 A | 7/1991 | Gamblin | |
| 5,205,499 A | 4/1993 | Gamblin | |
| 5,297,441 A * | 3/1994 | Smith et al. | 73/860 |
| 5,373,994 A | 12/1994 | Hunt | |
| 6,070,817 A | 6/2000 | Yanase | |
| 6,234,029 B1 * | 5/2001 | Liang et al. | 73/850 |
| 6,303,544 B1 | 10/2001 | Maas et al. | |

(Continued)

FOREIGN PATENT DOCUMENTS
GB    1586822 A    3/1981
(Continued)

OTHER PUBLICATIONS

K B Quast, Laboratory Studies in Comminution: Part VI The Specific Rate of Breakage for Rod and Ball Milling of Quartz, The AusIMM Proceedings, Dec. 31, 1998, pp. 1-7, vol. 303 (1), XP55016245.

(Continued)

*Primary Examiner* — Jewel V Thompson
(74) *Attorney, Agent, or Firm* — Bracewell & Giuliani LLP

(57) ABSTRACT

Methods and apparatuses are provided for testing and quantifying structural durability characteristics of bridging materials. Embodiments include sieving bridging materials to create uniform batches having particles within a predefined range. Embodiments further include selecting a batch and drying the batch, separating the dried batch into dry samples, and selecting a test sample having an initial mass. Embodiments include sealing the test sample, a volume of liquid, and a rod in a cylindrical testing cell and rotating the cylindrical testing cell containing the rod such that the rod rolls in relation to an inner wall of the cylindrical testing cell and applies force partially crushing the test sample. Embodiments further include sieving a resulting sample to create a durable sample having particles within the predefined range and drying the durable sample. Embodiments of methods further include measuring a mass of the dried durable sample to define a durable mass and comparing the durable mass to the initial mass.

36 Claims, 7 Drawing Sheets

U.S. PATENT DOCUMENTS

| | | | |
|---|---|---|---|
| 7,562,583 B2 * | 7/2009 | Conway et al. | 73/821 |
| 8,161,804 B2 * | 4/2012 | Herdzik et al. | 73/86 |
| 2009/0029878 A1 | 1/2009 | Bicerano | |
| 2009/0082229 A1 | 3/2009 | Dobson et al. | |
| 2010/0071902 A1 | 3/2010 | Ziegler et al. | |

FOREIGN PATENT DOCUMENTS

JP   53-121265 A   10/1978

OTHER PUBLICATIONS

International Search Report and Written Opinion of PCT Application No. PCT/US11/54894 dated Jan. 23, 2012.

Horton et al., "Enhanced Well Productivity Potential from a New High-Density Reservoir Drill-In Fluid", (2001), AADE-01-NC-OH-47.

Siddiqui et al., "Drill-in fluids for multi-lateral MRC wells in carbonate reservoir . . . ". 2006 SPE Asia Pacific Oil and Gas Conf. & Exhib., Adelaide, Australia, Sep. 11-13, 2008.

Amanullah, "A Novel Method of Assessment of Spurt and Filtrate Related Formation Damage of Potential of Drilling and Drill-in Fluids", SPE Asia Pacific Oil & Gas Conf & Exhib., Apr. 15-17, 2003, Jakarta, ID (SPE # 80464).

Amanullah, "A Novel Laboratory Method for Assessing the Erosional Characteristics of Mudcakes", SPE Production and Operations, May 2006, pp. 245-251.

Suri et al, "Strategies for Sizing Particles in Drilling and Completion Fluids", SPE Journal (Mar. 2004), pp. 13-23.

Vickers et al., "A new methodology that surpasses current bridging theories to efficiently seal a varied pore throat distribution as found in natural reservoir formations", AADE 06-DF-HO-16 (2006).

* cited by examiner

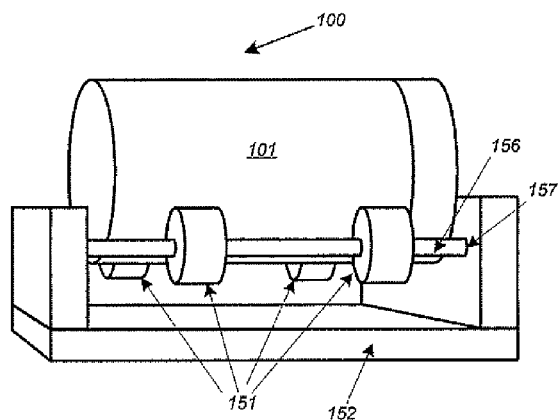 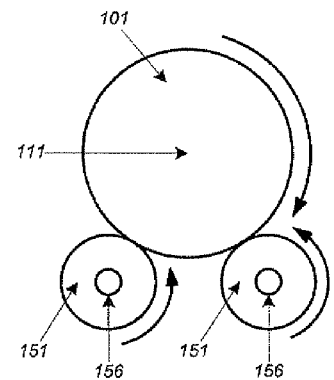
FIG. 3A	FIG. 3B
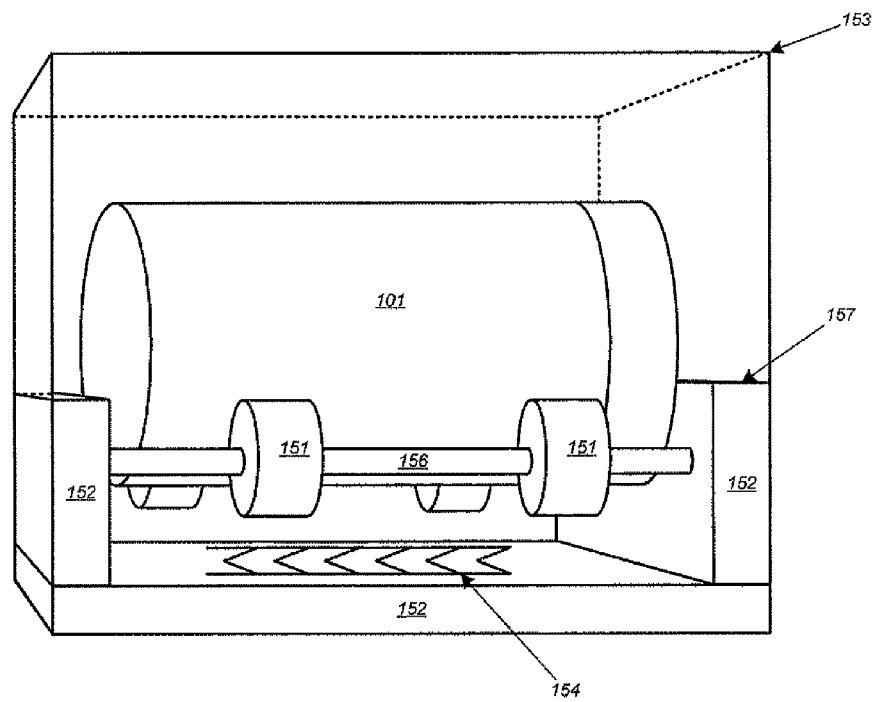
FIG. 3C

METHOD AND APPARATUS FOR QUALITY CONTROL AND QUALITY ASSURANCE OF SIZED BRIDGING MATERIALS USED IN DRILL-IN FLUID FORMULATION

BACKGROUND OF THE INVENTION

1. Area of the Invention

The present invention relates to drill-in fluids used in oil and gas drilling. More specifically, the present invention relates to bridging materials used in the formulation of drill-in fluids. The present invention relates to a laboratory method, the "Aramco Method," for evaluating the durability of sized bridging materials used in the formulation of drill-in fluid to eliminate or minimize formation damage.

2. Description of the Related Art

A drill-in fluid is a special type of fluid formulated for oil and gas drilling. The drill-in fluid is pumped into a borehole while drilling through porous and permeable subsurface rock formations that store and transmit oil and gas, i.e., a reservoir. The drill-in fluid contains solid particles known as bridging materials to prevent fluid loss from the borehole to the reservoir by building a "filter cake" for preventing fluid loss into the reservoir.

Bridging materials are solid particles, typically composed of calcium carbonate ($CaCO_3$), dolomite, or marble, and are designed to "bridge" across the pore throat or fractures in the vicinity of the borehole wall. Bridging materials can produce a low-permeability mud-cake on the borehole wall to minimize fluid leak-off, eliminate spurt loss, arrest migration of fine particles ("fines") into the reservoir or formation, prevent mud-cake deposition into the formation, and inhibit near-wellbore formation damage. The fluid formulation containing the bridging materials, which may be referred to as a "mud," can be tailored to specific geological applications by tailoring the size range of the bridging materials to achieve a desired fluid density and bridging ability. For example, one can select bridging materials manufactured to certain sizes (coarse, medium, fine, and very fine) to achieve a particular size-distribution scheme corresponding to the pore throat sizes of a target reservoir.

The effectiveness of bridging materials depends on their structural durability, as they are subject to damage due to extreme conditions during the drilling operation (i.e., "downhole conditions"). For example, bridging materials can disintegrate, decompose, and disperse as a result of physical interactions with a drill bit, tool joint, reamer, stabilizer, mud motor stator and blades, and bend drill string. When the bridging materials decompose into smaller and finer particles, the intended distribution scheme is lost, destroying the desired fluid properties and bridging abilities. For example, there can be a dramatic change in the particle size distribution curve.

The smaller, finer particles resulting from the decomposition of bridging materials can also harm the drilling operation. For example, the loss of the drilling fluid's bridging ability may result in the migration of drilling fluids into the reservoir. And after migrating into the formation, the bridging materials, including the fine particles created when bridging materials decompose, can create deposits that damage the reservoir and significantly reduce the production capability of a well. Although properly sized bridging materials are very useful in plugging and sealing fractures and openings in a borehole wall to create a tight and low-permeability mud-cake, failure to maintain the intended size distribution while drilling may be a severe cause of near-wellbore formation damage.

The importance of using of a particular particle size distribution of bridging materials that is compatible to the pore throat size distribution of the target reservoir is well known to the industry. The industry is also aware of the importance of preserving the particle size distribution ("PSD") while drilling to get the maximum benefit of the drill-in fluid. However, there is no industry method or standard test method to monitor the PSD while drilling or to screen and evaluate different bridging materials as a part of quality control/assurance procedures or as part of selecting optimal bridging materials (i.e., materials with an optimal durability index). Horton et al. (Horton, R. L., Dobson, J. W. Jr., Tresco, K. O., Knox, D. A., Green, T. C. and Foxenberg, W. E. (2001), Enhanced Well Productivity Potential from a New High-Density Reservoir Drill-in Fluid, AADE 01-NC-OH-47) described the importance of using an optimum amount of sized bridging materials and an optimum PSD in drilling and drill-in fluids to control the thickness, porosity, and permeability of deposited mud-cake, reduce the loss of mud filtrate into the near wellbore formation, and facilitate the effective cleaning of the mud-cake from the borehole wall.

Siddiqui et al (Siddiqui, M. A., Al-Ansari, A. A., Al-Afaleg, N. I., Al-Anazi, H. A., Hembling, D. E., and Bataweel, M. A. (2006), Drill-in Fluids for Multi-lateral MRC Wells in carbonate Reservoir—PSD Optimization and Best Practices Lead to High Productivity: A case Study. 2006 SPE Asia Pacific Oil and Gas Conf. & Exhb., Adelaide, Australia, 11-13 September, SPE#101169) described less-damaging water-based drill-in fluids for use in multilateral maximum reservoir contact wells. The authors optimized the particle size distribution using fine and medium-sized particles of calcium carbonate with fairly fixed median value to reduce formation damage caused by fines and polymer plugging. According to their study, the optimum ratio of fine to medium-sized calcium carbonate was 35:65 (8:15 ppb fine:medium) in 23 ppb bridging material loaded drill-in fluid. Tests conducted using a reservoir core and a dynamic mud flow loop at stimulated reservoir conditions resulted in 20% loss in return permeability in the presence of the size optimized drill-in fluid. The use of this size optimized drill-in fluid enhanced the well productivity significantly. The authors also emphasized the need for maintaining the designated particle size distribution in the drill-in fluid while drilling to maximize reservoir protection capacity.

According to Suri and Sharma (Suri, A. and Sharma, M. M. (2004)), Strategies for Sizing Particles in Drilling and Completion Fluids, SPE Journal, March, pp. 13-23, the sized particles used in drilling and completion fluids to minimize formation damage must be large enough to stay at the borehole wall and small enough to form a tight filter cake that effectively prevents the invasion and internal mudcake formation by any solids and polymers in the near wellbore reservoir. Modeling done by the authors based on this criterion demonstrated the usefulness of this criterion for quantitative determination of the particle size distribution necessary to design a drill-in fluids for a given formation permeability and overbalance pressure. According to the authors, the predictions of the model agree well with the results of mud filtration experiments.

According to Vickers et al (Vickers S., Cowie M., Jones T., Tywnam, A. J. (2006)), a new methodology that surpasses current bridging theories to efficiently seal a varied pore throat distribution as found in natural reservoir formations, AADE 06-DF-HO-16, selection and maintenance of five different particle sizes with respect to the measured pore throat size distribution of the formation core are necessary in order to create a tightly packed mudcake on the borehole wall. This size distribution is required to match separately the different pore throat sizes to produce a "jamming effect" by bridging or filling the fracture openings and inter-particle gaps of all sizes. According to the authors, a particle size such as D90 should be less than the largest pore throat size, D75 should be less than 2/3 of the largest pore throat, D50 should be ±1/3 of the mean pore throat size, D25 should be 1/7 of the mean pore throat size, and D10 should be greater than the smallest pore throat size. Laboratory and field tests demonstrated the effectiveness of this particle size distribution pattern in bridging openings and preventing formation damage compared to other methods of particle size selection. According to the authors this method is equally applicable for both oil-based and water-based muds.

The importance of maintaining the intended particle size distribution during drilling operations highlights the need for a simple, reliable, accurate, and statistically valid method for screening, quality control, and quality assurance of bridging materials used for drill-in fluid formulation.

Variation in the composition of bridging materials is common due to different grinding procedures and equipment used in the process of manufacturing the bridging materials. Due to variations in the composition and manufacturing of bridging materials, there is a wide variation in their structural durability in operation. For example, particle angularity, morphology, raw material quality, internal damage to the fabric and structures of the bridging materials play an important role in the overall behavior of the materials when subject to forces in the downhole environment. Also, there are variations in the sources of physical, chemical, mechanical, and geological characteristics; degree of purity; and level of compliance with manufacturer's quality assurance measures among bridging materials. Because of the wide variation in the mechanical durability of bridging materials in downhole conditions, the identification and selection of highly durable bridging materials is critical in formulating drilling fluids to minimize formation damage while drilling. The art provides no suitable methodology or tools to simulate downhole conditions and so that the durability of bridging materials can be tested and quantified.

SUMMARY OF THE INVENTION

Applicants appreciate the importance of selecting bridging materials as described herein and have provided methods and apparatuses that can be instrumental in minimizing formation damage associated with drill-in fluids in general and bridging materials in particular.

Applicants recognize that is useful to have appropriate particle size distribution with some overlapping of the sized particle ranges from very fine, fines, medium, and course to bridge the variable openings of a reservoir formation. Applicants also recognize the importance of optimizing a particle size distribution for given formation with a particular pore throat size distribution so as to minimize mud-induced formation damage. Optimized concentrations and particle size distributions of acid-soluble salts such as calcium carbonate or some water-soluble salts such as sodium chloride, potassium chloride, magnesium chloride, etc, are provided by different service providers. These sized mud additives, however, are manufactured by using various grinding procedures and equipment and result in divergent product quality. Applicants recognize that poor quality control of the product, such as particle angularity, morphology, raw material quality, internal damage to fabric and structures during grinding and crushing, etc., play an important role in overall behavior of the materials. Applicants further recognize that, although properly sized bridging materials are useful in plugging and sealing fractures and openings of borehole walls to create a tight and low-permeable mudcake, failure to maintain the intended particle size distribution may be a severe cause of near wellbore formation damage while drilling. Applicants further recognize that failure to monitor the changes in particle size distribution and lack of any remedial action to correct it may lead to severe formation damage as a result of reduction of the median particle size of the bridging materials due to crushing and grinding action of the down hole tools and equipment. Furthermore, applicants recognize that the importance of particle size distribution and the necessity to preserve this particle size distribution of bridging materials presents a need in the art for a simple, reliable, accurate, and statistically valid method for screening, quality control, and quality assurance of bridging materials used for drill-in fluid formulations.

Applicants also recognize the instability in particle size distribution arises due to the easy disintegration and dispersion of poor quality bridging materials in down hole conditions due to the physical interactions with a drill bit, tool joint, reamer, stabilizer, mud motor stator and blades, bend drill string in case of horizontal, extended reach, and multilateral drilling operations—producing a dramatic change in the PSD, PSD curve, and particle size cut points. Applicants recognize the need in the industry for a suitable methodology to characterize bridging material products as a part of a quality control or quality assurance process and as a strategic tool to select the best product to minimize formation damage while drilling.

Applicants have performed innovative research leading to the development of a suitable methodology for routine screening and evaluation of the quality of different bridging materials (sized particles) used to prevent fluid-induced formation damage while drilling into a reservoir.

Embodiments of methods and apparatuses according to the present invention provide a decision-making tool to the industry to select the best bridging material to prevent formation damage, for example, by fluid leak-off, mud spurt invasion, and internal mudcake formation. Embodiments of methods and apparatuses according to the present invention provide a simple, reliable, accurate, and statistically valid framework for simulating downhole tool interactions and wet grinding actions of a borehole environment. Embodiments of the present invention further provide methods and apparatuses for testing the durability of sized bridging materials by simulating downhole tool interactions and wet grinding actions of a borehole environment. In particular, embodiments of the present invention provide methods and apparatuses to quantify the durability of sized bridging materials and distinguish variations in the durability characteristics of different bridging materials responsive to simulating downhole tool interactions and wet grinding actions of a borehole environment.

Embodiments of the present invention provide methods and apparatuses for testing and quantifying the durability of sized bridging materials to enhance the quality control and quality assurance process in manufacturing bridging materials and to enhance the screening and selection of bridging materials in formulating drill-in fluids for oil and gas drilling operations. For example, such embodiments allow for routine quality assurance/control screening and evaluation of bridging materials by a manufacturer, a supplier, a distributor, or a customer so that the durability of bridging materials may be quantified according to a standard procedure.

Embodiments of the present invention provide a test method to measure the hardness-related durability of sized bridging materials, for example, calcium carbonate chips using conventional mud equipment, by simulating downhole tool interactions, for example, through wet grinding actions. Embodiments of the present invention can provide a metric to quantify the durability of sized bridging materials that allows a qualitative comparison to be made between different bridging materials to determine which would suffer the least amount of size degradation while drilling. Accordingly, the hardness-related durability of sized bridging materials can be measured and quantified independently from any fluid properties (rheological properties and viscosity properties) of formulations of such bridging materials, for example, drilling muds.

Embodiments of the present invention can account for the factors that play a significant role in the wet grinding process of the downhole environment and can provide an aggressive wet grinding test to reflect the "worst ease" scenario in the downhole environment.

Embodiments of the present invention allow for a simple laboratory-based or field-deployable, i.e., bench-sized, apparatus and method to evaluate the relative durability of sized bridging materials used in drill-in fluids, the method requiring no special skill or experience to perform.

A method according to an embodiment of the invention is provided for testing and quantifying structural durability characteristics of sized bridging materials. Such a method can include the step of sieving a bulk of the sized bridging materials to create a plurality of uniform batches, each uniform batch having particles within a predefined range. Such a method can further include the step of selecting a primary uniform batch and drying the primary uniform batch to remove residual moisture in the primary uniform batch to create a dry uniform batch. Such a method can further include the step of separating the dry uniform batch into a plurality of dry samples. Such a method can further include the step of selecting a dry sample from the plurality of dry samples to define a test sample, the test sample having an initial mass.

Also according to an embodiment of the invention, such a method can further include the step of sealing the test sample, a preselected volume of liquid, and a loose cylindrical rod in a cylindrical testing cell, the cylindrical testing cell having a substantially cylindrical inner wall. Such a method can further include the step of rotating the cylindrical testing cell containing the loose cylindrical rod such that the loose cylindrical rod rolls in relation to the cylindrical inner wall of the cylindrical testing cell, the loose cylindrical rod applying force to the test sample such that the test sample is partially crushed into a resulting sample.

Also according to an embodiment of the invention, such a method can further include the step of sieving the resulting sample to create a durable sample having particles within the predefined range. Such a method can further include the step of drying the durable sample to remove residual moisture in the durable sample to create a dry durable sample.

Also according to an embodiment of the invention, such a method can further include the step of measuring the mass of the dry durable sample to define a durable mass. Such a method can further include the step of comparing the durable mass to the initial mass.

BRIEF DESCRIPTION OF THE DRAWINGS

So that the manner in which the features and advantages of the invention, as well as others which will become apparent are attained and can be understood in more detail, a more particular description of the invention briefly summarized above may be had by reference to the embodiment thereof which is illustrated in the appended drawings, which drawings form a part of this specification. It is to be noted, however, that the drawings illustrate only an embodiment of the invention and therefore are not to be considered limiting of its scope as the invention may admit to other equally effective embodiments.

FIG. 3A is a schematic drawing of an oblique view of an apparatus according to an embodiment of the present invention.

FIG. 3B is a schematic showing a radial cutaway of an apparatus according to an embodiment of the present invention.

FIG. 3C is a schematic drawing of an oblique view of an apparatus according to an embodiment of the present invention.

DETAILED DESCRIPTION OF THE INVENTION

Figure 1A:
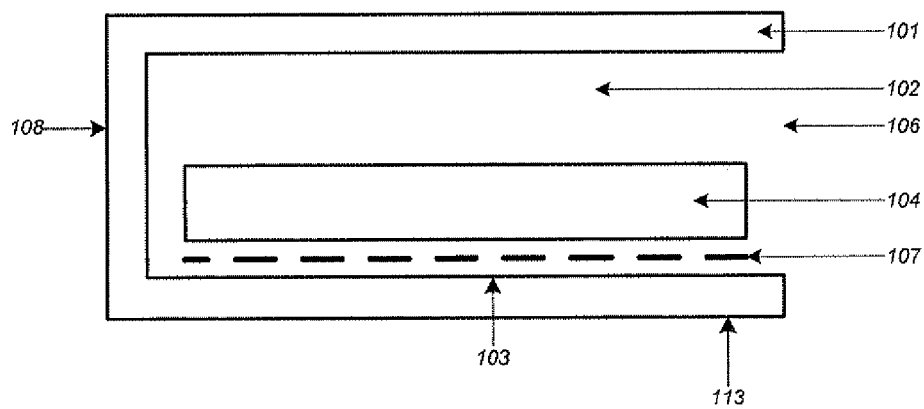
FIG. 1A is a schematic showing an axial cutaway of an apparatus according to an embodiment of the present invention.

Embodiments of the present invention include an apparatus for testing structural durability characteristics of sized bridging materials by simulating downhole tool interactions and wet grinding actions upon sized bridging materials. The apparatus 100 can be shown with reference to FIG. 1A, FIG. 1B, FIG. 2A, and FIG. 2A. The apparatus 100 includes a cylindrical tubular container 101 having an outer surface 101 that is substantially cylindrically shaped. As can be shown with reference to the cross-section of FIG. 1A, the tubular container 101 is hollow, and the open space 102 within the tubular container 101 is bound by an inner surface 103 of the tubular container. The inner space 102 of the tubular container 101 is also of a substantially cylindrical shape, and is defined herein as a testing cell 102.

The tubular container 101 also has two ends 108 and 106 that correspond to bases of the cylindrical shape of the tubular container 101. A major axis 111 of the tubular container 101, as can be shown with respect to FIG. 1B, corresponds to the axis of the cylinder represented by the substantially cylindrical shape of the tubular container 101, and the major axis 111 intersects the centers of the bases of the cylindrical shape of the tubular container 101, as is shown in FIG. 1B. End 108 of the tubular container 101 can be, for example, a closed end having a sealing cap positioned thereon in any manner that will be appreciated by those having skill in the art so that the sealing cap can be permanently or non-permanently attached to or integrally joined with the tubular container 101 to close the end 108 of the tubular container 101. The sealing cap may be, for example, screwed, pressed, or otherwise permanently or non-permanently attached to the tubular container 101 at the end 108. End 106 of the tubular container 101 can be, for example, an open end or a closed end having a removable sealing lid 109, as can be shown with respect to FIG. 2A. The removable sealing lid 109 can be screwed onto or positioned thereon in any manner known to those skilled in the art so that the sealing cap can be non-permanently attached to the tubular container 101 to close the end 106 of the tubular container 101. The sealing lid 109 may be, for example, screwed, pressed, or otherwise non-permanently attached to the tubular container 101, according to techniques that will be appreciated by those having skill in the art. As can be shown in FIG. 1A, the testing cell 102 can be physically accessible at the open end 106 of the tubular container 101 when the removable sealing lid 109 is removed.

Figure 2B:
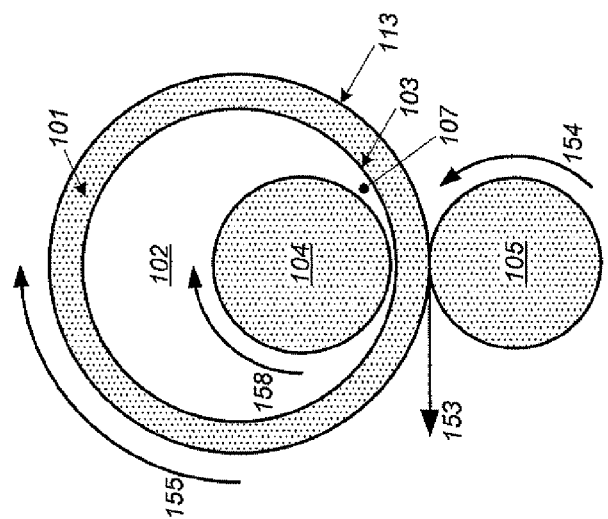
FIG. 2B is a schematic showing a radial cutaway of an apparatus according to an embodiment of the present invention.
Figure 2A:
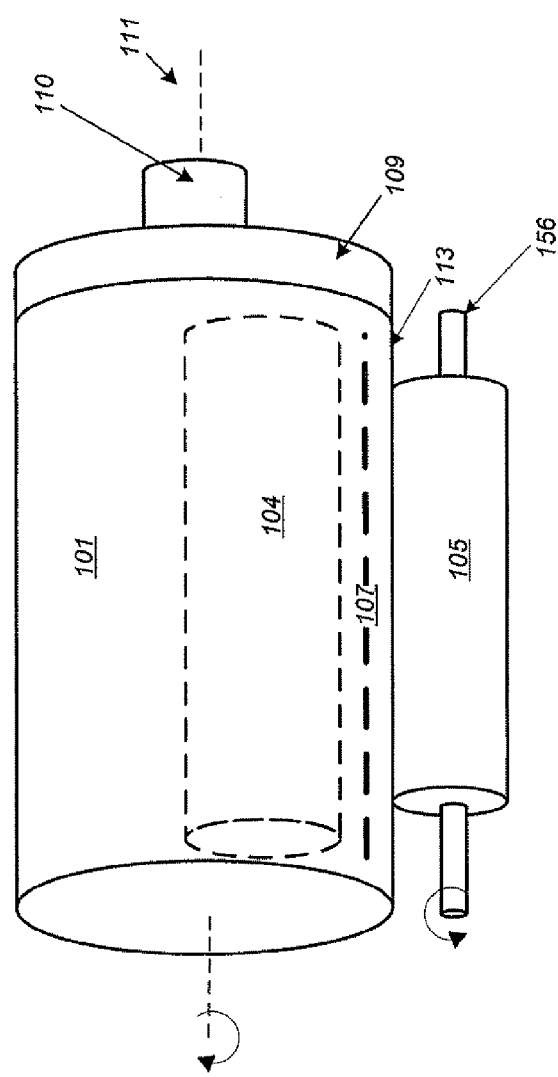
FIG. 2A is schematic showing an oblique transparency view of an apparatus and two axes of rotation therein according to an embodiment of the present invention.

As can be shown with respect to FIG. 2A, the apparatus 100 also includes a roller 105 to rotate the tubular container 101. The roller 105 can positioned to apply force to the tubular container 101 so that the tubular container 101 rotates about its major axis 111. In one embodiment, the roller 105 rotates 154 about an axle 156, the roller 105 being in physical contact with the outer surface of the tubular container 101 while the major axis 111 of the tubular container 101 is positioned horizontal and substantially parallel to the axle 156 for the roller 105. As can be shown with respect to FIG. 2B, the rotation 154 of the roller 105 while in physical contact with the outer wall of the tubular container 101 causes the roller 105 to apply a force 153 to the outer wall of the tubular container 101 that causes the tubular container 101 to rotate 155 about its major axis 111. Those having skill in the art will understand any of various measures that can be employed to stabilize the roller 105 and the tubular container 101 so that the roller 105 and the tubular container 101 remain in physical contact while the tubular container 101 rotates about its major axis. For example, as illustrated in FIG. 3 and FIG. 3B, the tubular container 101 can be positioned horizontally upon on several rollers 151 so that the tubular container 101 is entirely supported by the rollers 151 while the tubular container 101 rotates about its major axis. Axles 156 for the rollers 151 can be positioned in a fixed structure 152, for example, using bushings to allow rotation of the axles 156 within the fixed structure 152. The roller 105 can be driven by an electric motor 351, as can be shown with respect to FIG. 4, according to drive configurations known to those having skill in the art. The electric motor 351 can also be attached to a fixed structure 152, and the motor 351 can provide a torque to the axles 156, for example, rotate the roller 105, causing the tubular container 101 to rotate about its major axis. The rotational speed for rotating the roller 105, as is described further herein, shall be sufficient to allow simulated downhole tool interactions within the tubular container 101 but shall not exceed a speed that allows the tubular container 101 to remain positioned on the rollers 151 during rotation.

Figure 1B:
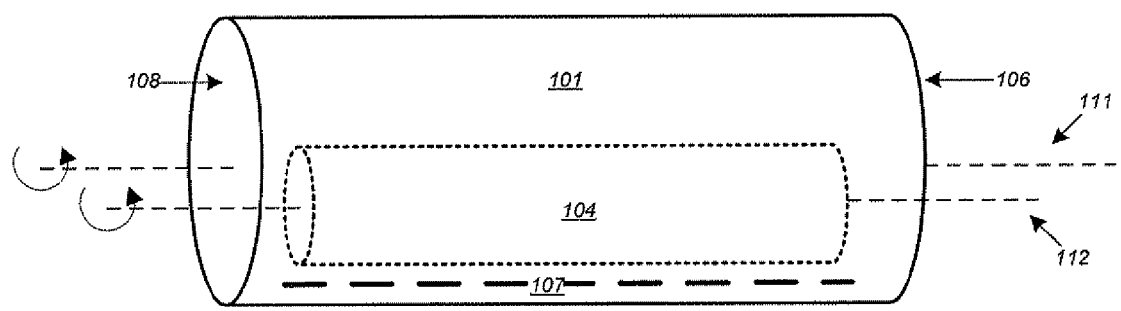
FIG. 1B is schematic showing a transparency view of an apparatus and two axes of rotation therein according to an embodiment of the present invention.

As can be shown with reference to FIG. 1A, FIG. 1B, FIG. 2A, and FIG. 2B, the apparatus 100 further includes a loose cylindrical rod 104 positioned in the testing cell 102 so that the loose cylindrical rod 104 is supported within the testing cell 102 when the loose cylindrical rod 104 rests along the lowest portion of the cylindrical inner wall 103 of the testing cell 102 positioned horizontally. Because the loose cylindrical rod 104 is loose, it can roll freely along the cylindrical inner wall 103 of the testing cell 102 when the tubular container 101 rotates about its major axis, as has been described herein. The position of the loose cylindrical rod 104 in the testing cell 102, as is shown in FIG. 2B, can remain substantially near the bottom of the testing cell 102 during the rotation of the tubular container 101. A major axis 112 of the loose cylindrical rod 104, as can be shown with respect to FIG. 1B, corresponds to the axis of the cylindrical shape of the loose cylindrical rod 104 and the major axis 112 intersects the centers of the bases of the cylindrical shape of the loose cylindrical rod 104. As is shown in FIG. 1A and FIG. 1B, the loose cylindrical rod 104 can be positioned in the testing cell 102 so that the major axis 112 is substantially parallel to the major axis 111 of the tubular container. For example, loose cylindrical rod 104 and testing cell 102 are positioned horizontally in FIG. 1A and FIG. 1B and the loose cylindrical rod 104 is positioned on the cylindrical inner wall 103 of the testing cell 102.

As can be shown with reference to FIG. 2A, the apparatus 100 can further include a sealing lid 109 positioned on the tubular container 101 to cover the open end 106 of the tubular container 101. The sealing lid 109 can be a removable unit or assembly that can be attached to the tubular container 101 at the open end 106 of the tubular container 101 to enclose and seal the contents of the testing cell 102, including the loose cylindrical rod 104 and any other contents placed therein, such as sized bridging materials 107 and liquid. The sealing lid 109 can be attached to the tubular container as will be appreciated by those skilled in the art, including using a threaded screw-on attachment wherein the tubular container 101 and the sealing lid 109 have compatible threads, for example. In certain embodiments, the removable sealing lid 109 can include a relief valve 110 to allow room temperature conditions or high temperatures and high pressures within the testing cell 102. The relief valve can be, for example, a stem valve manufactured by OFI Testing Equipment, Inc. of Houston, Tex.

The apparatus 100 can have preselected dimensions within a range of dimensions to allow or enhance a bench-sized simulation of downhole tool interactions and wet grinding actions of a borehole environment within the testing cell 102. The preselected dimensions also shall allow the stability of the tubular container 101 and the position of the loose cylindrical rod 104, as described herein, during rotation of the tubular container 101. The dimensions of the testing cell 102 and the loose cylindrical rod 104, for example, can be preselected to enhance the simulation of downhole tool interactions and wet grinding actions of a borehole environment upon a sample of sized bridging materials 107 positioned within the testing cell 102, as is shown in FIG. 1A, FIG. 1B, FIG. 2A, and FIG. 2B. For example, the testing cell 102 can have a volume of 400 cubic centimeters (cc) or greater, a mass in the range of 3,200 to 3,300 grams, a length in the range of 7.0 to 8.0 inches, and a diameter in the range of 2.25 to 2.75 inches. Also, for example, the loose cylindrical rod 104 can be cut or milled of solid steel and have a mass in the range of 550 to 600 grams, a length of 6.0 to 6.25 inches, and an outer diameter in the range of 1.0 to 1.5 inches. For example, the sealing lid 109 can have a height in the range of 0.5 to 0.75 inches, a diameter of 3.00 to 3.25 inches, and a mass of 575 to 600 grams; and the relief valve 110 can have a length of 1.75 to 2.00 inches, a diameter of 0.25 to 0.50 inches, and a mass of 15 to 20 grams.

Figure 4:
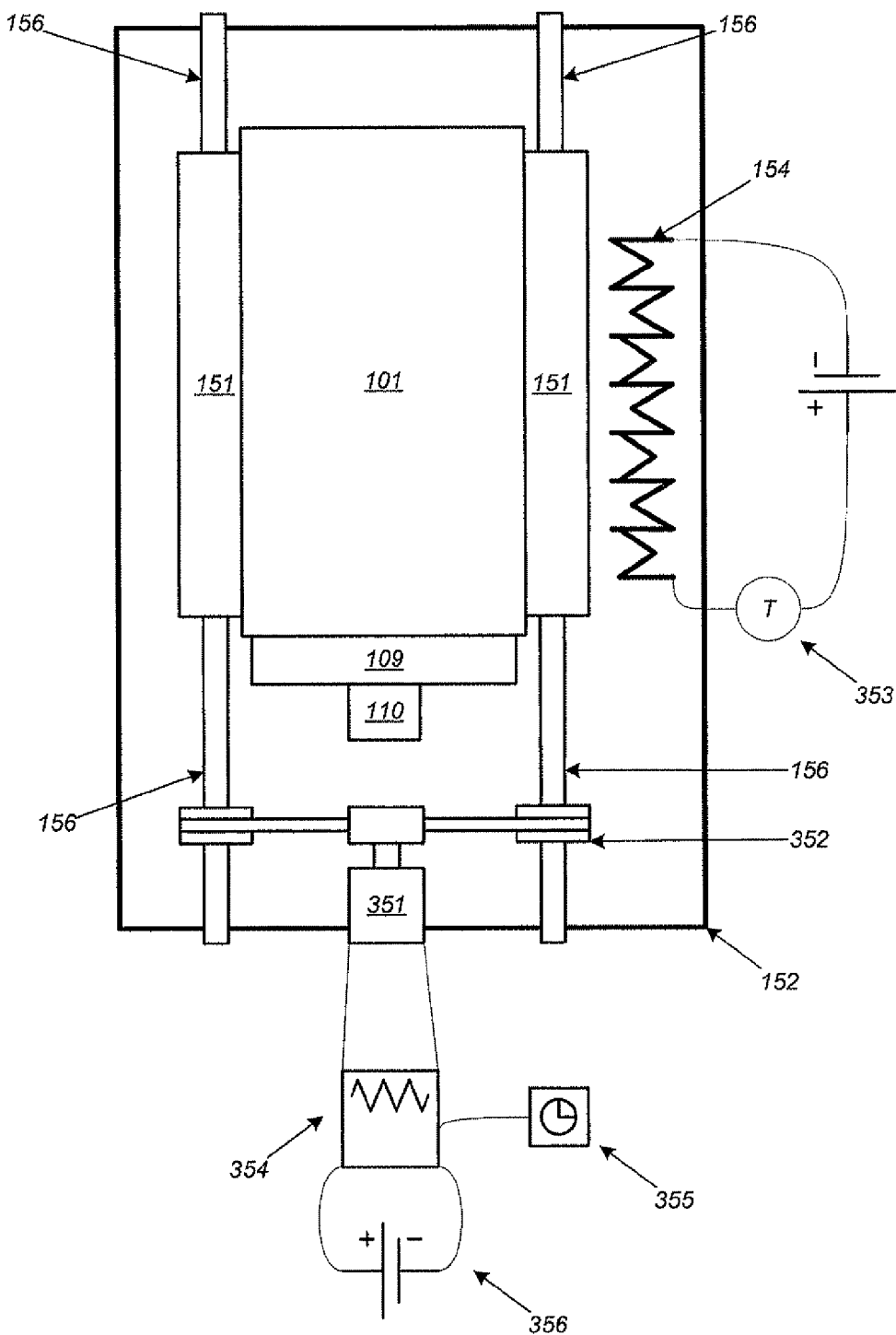
FIG. 4 is a schematic showing of a top or layout view of an apparatus according to an embodiment of the present invention.
Figure 5:
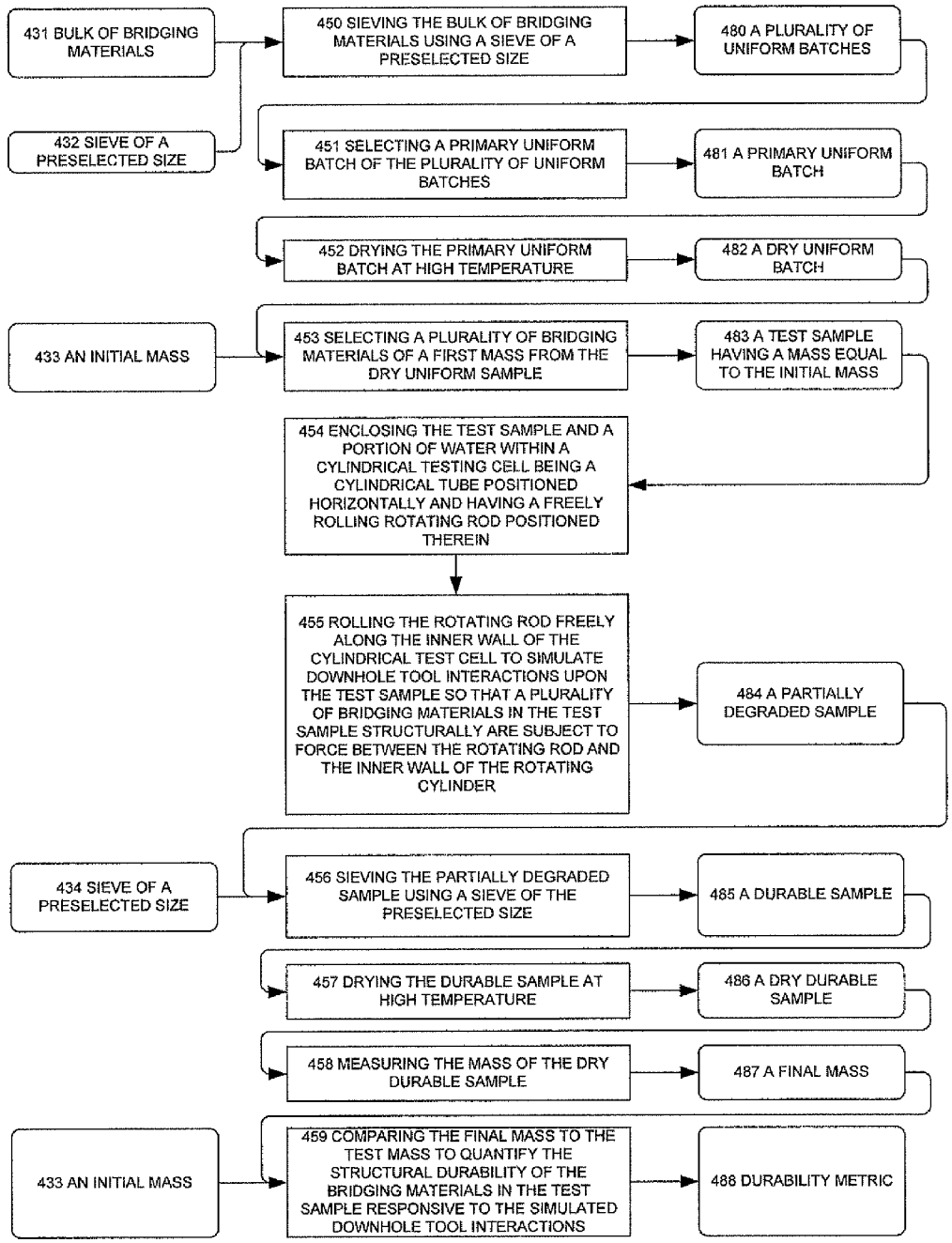
FIG. 5 is a flowchart showing steps and products of methods according to an embodiment of the present invention.

The apparatus 100 can further include a temperature-controlled rolling environment 153 as can be shown with reference to FIG. 3C and FIG. 4. The temperature-controlled rolling environment 153 can include an insulated shell, for example, that attaches to the fixed structure 152 so as to enclose the tubular container 101 and maintain a preselected temperature to enhance the simulation of downhole tool interactions and wet grinding actions of a borehole environment upon a sample of sized bridging materials 107 positioned within the testing cell 102. The temperature-controlled rolling chamber 153 can include, for example, an insulated shell, a heating element 154 inside the insulated shell, and a thermostat 353 to control the temperature of the heating element. Insulated shell 156 can be constructed, for example, using stainless steel. The insulated shell 156 can include, for example, insulated gasket 157 between the insulated shell 154 and the fixed structure 152. In one embodiment, as illustrated in FIG. 3C, the heating element 154, for example, can include an electric heating coil positioned within the insulated shell and capable of heating the tubular container 101 by convection. In other embodiments, the heating element 154, for example, can include heating coils positioned within a roller 105 capable of heating the tubular container 101 by conduction. The thermostat 353, as will be appreciated by those having skill in the art, can be set to a preselected temperature, for example, by a human operator, and control the temperature of the tubular container 101 or the testing cell 102 by adjusting the output of the heating coil 154 so that the preselected temperature is achieved. Thermostat 353 can be, for example, an electronic solid state thermostat manufactured or provided by OFI Testing Equipment, Inc. of Houston, Tex.

The apparatus 100 can further include a speed controller 354 and a timer 355 to drive the motor at a preselected speed for a preselected time. The motor can be, for example, any sort of alternating current (AC), direct current (DC), or universal electric motor driven by an electrical current source 356, the speed controller 354 can be any sort of electric or mechanical speed controller, such as a thyristor circuit, for example, as will be known to those having skill in the art.

Those of skill in the art will appreciate that a motor 351 and the speed controller 354 can be selected that are capable of rotating the testing cylinder 101 at a speed in the range of 25 to 35 revolutions per minute, as such rotational speed is desirable for effectively simulating grinding actions within the testing cell 102. The motor 351 can be, for example, an electric motor model "174-13" manufactured or provided by OFI Testing Equipment, Inc. of Houston, Tex. The speed controller 355 can be, for example, controller model "174-14" manufactured or provided by OFI Testing Equipment, Inc. of Houston, Tex.

Embodiments of the present invention also include methods for testing the hardness-related structural durability characteristics of sized bridging materials by simulating downhole tool interactions and wet grinding actions upon sized bridging materials. The methods can be shown with reference to FIG. 5, FIG. 7A, FIG. 7B, and FIG. 7C.

Embodiments of methods according to the present invention include sieving 450 a bulk of bridging materials 431 to create a plurality of uniform batches 480. The bulk of bridging materials 431 can include a mass of sized bridging materials, for example, of approximately 2 kilograms in total. The bulk of bridging materials 431 can include solid particles, typically composed of calcium carbonate ($CaCO_3$), dolomite, or marble, which are designed to "bridge" across the pore throat or fractures in reservoir rock when formulated in a drill-in fluid and used in oil and gas drilling operations. The fluid formulation containing the bridging materials, which may be referred to as a "mud," can be tailored to specific geological applications by employing a tailored range of the bridging material sizes to achieve a desired fluid density and bridging ability. Bridging materials 431 can be manufactured to certain sizes such as coarse, medium, fine, or very fine, which allows the selection of a particular size distribution scheme corresponding to the pore throat sizes of a target reservoir. Each uniform batch of the plurality of uniform batches includes particles within a predefined range of sizes.

The step of sieving 450 the bulk of bridging materials may include using a sieve, or sieves of a preselected size 432 or preselected sizes. The preselected sieve 432 can be any commercially available sieve of a preselected size corresponding to the size of the bridging materials that are desired to be tested, such as a 600 micron sieve, for example. The sieve may also be, for example, any of different sized sieves at or below 1000 microns. As will be appreciated by those skilled in the art, sieving may require the use of a blank or pan and a sieve shaker. Responsive to the sieving step 450, a uniform batch can be created wherein all particles therein are of a size within a predefined range of sizes corresponding to the size of the sieve or sieves used. The uniform batch 481 will contain bridging materials 431 of a size corresponding to the size of the sieve, for example, a uniform 600 micron size. By way of further example, the step of sieving 450 can include sieving a representative amount of the sized materials to determine cut-point particle sizes of 600+, 425+, and 212+ microns.

Embodiments of methods according to the present invention can also include selecting 451 a primary uniform batch 481 of the plurality of uniform batches 480. Also by way of example, more than 200 grams of 600+, 425+, and 200+ micron bridging materials can be selected from the bulk mass using a sieve shaker and the appropriate sieve size. The cut-point samples can be dried, leveled, and stored for testing, as is described herein. The primary uniform batch 481 can have of a mass sufficient to perform multiple iterations of steps of the method using a test sample, as described herein, to allow for averaging the results of the method for multiple iterations, for example, a cut point sample of approximately 200 gm to perform 6 or more iterations of the method as described further herein.

Embodiments of methods according to the present invention can also include drying 452 the primary uniform batch 481 at high temperature to create a dry uniform batch 482. As will be appreciated by those skilled in the art, the drying operation can be performed by any drying apparatus known to those of skill in the art, including, for example, an oven or micro-oven having a temperature controller and being capable of maintaining a constant temperature during the operation of drying the sized bridging materials in the primary uniform batch 481. The oven can be, for example, a 115 volt gravity convection drying oven, model "174-50", manufactured or provided by OFI Testing Equipment, Inc. of Houston, Tex. In certain embodiments of the present invention, for example, the drying operation can be performed at 105 degrees Celsius and for a period of four or more hours. The drying operation can be performed so that the sized bridging materials in the dry uniform batch achieve a consistent and minimal level of residual moisture therein, which allows for accurately and consistently measuring the mass or weight of the sized bridging materials therein without introducing error due to residual moisture.

Embodiments of methods according to the present invention can also include separating the dry uniform batch 482 into a plurality of dry samples and selecting 453 a dry sample from the plurality of dry samples to define a test sample 483, the test sample having an initial mass 433. The separating operation can include, for example, measuring off a portion of a given mass, e.g., the initial mass 433, of the dry uniform batch 482. The plurality of dry samples can be separated according to mass, for example, using techniques that will be appreciated by those having skill in the art, such as by using a balance or a digital balance. The initial mass 433 can be used in a later step 459 of the method, for example, to determine a durability metric 488 of the bridging materials 431. The initial mass 433 can be, for example, 25 grams and the test sample 483 can be, for example, 25 grams of dry 600+ micron bridging materials of the dry uniform batch 482.

Embodiments of methods according to the present invention can also include test steps which may simulate downhole tool interactions upon the test sample so that the effects of the downhole tool interactions upon the test sample, as solid particles, can be measured, specifically by measuring the amount of the test sample that did not decompose or decay as a result of the simulated downhole tool interactions. As is described further herein, embodiments of methods according to the present invention can, for example, simulate bit grinding effects, bit nozzle impact, mud motor impact, and hydrodynamic shearing action of downhole fluids, tools, and equipment.

To simulate downhole tool interactions upon the test sample, the test sample 483 and a preselected volume of liquid, and a loose cylindrical rod 104 can be enclosed 454 in a substantially cylindrical testing cell 102, defined as a testing cell, having an interior that is also substantially cylindrical in shape. The cylindrical testing cell 102 can be included in a tubular container 101 as illustrated in FIG. 2A. The enclosing 454 of the test sample 483 can include sealing the testing cell using a sealing lid 109 as illustrated in FIG. 1A. The loose cylindrical rod 104 can be positioned in the testing cell 102 as can be shown with respect to FIG. 1A and FIG. 1B so that the testing cell 102 and the loose cylindrical rod 104 are positioned substantially parallel and horizontal and the loose cylindrical rod 104 can freely rotate about its horizontal axis with respect to the cylindrical inner wall 103 of the testing cell 102, as can be shown with respect to FIG. 2A and FIG. 2B. Certain embodiments can include enclosing 454 the test sample 483 in the testing cell 102 only after the loose cylindrical rod 104 has already been inserted into the testing cell 102 to decrease the likelihood that the bridging materials in the test sample 483 are prematurely broken, for example, by the loose cylindrical rod 104 being dropped into the testing cell 102 with the test sample 483 already positioned therein. In the event that bridging materials in the test sample 483 are prematurely broken, there is a risk of bias or error in the durability metric 488.

The preselected volume of liquid enclosed in the testing cell 102 can be, for example, 250 milliliters of tap water, which can be positioned in the testing cell 102 after the test sample 483 has been positioned therein. Tap water, for example, is able to enhance the simulation of the downhole tool interactions, particularly, with respect to an aggressive wet grinding action. Other fluids, such as sea water, salt water, simulated pore fluid, diesel, mineral oil, synthetic oil, esterified oil, or vegetable oils can also be used as the preselected volume of liquid to simulate downhole tool interactions and wet grinding. Any of the foregoing liquids, for example, may be sufficient for simulating downhole tool interactions and wet grinding actions without the addition of chemicals intended to react with a formulation of the bridging materials in the liquid. Embodiments of methods according to the present invention can be used to test the durability of bridging materials for both oil-based and water-based muds.

Figure 7A:
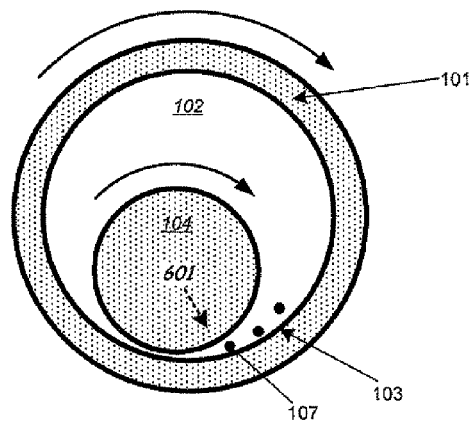
FIG. 7A is a schematic drawing showing methods according to an embodiment of the present invention.
Figure 6:
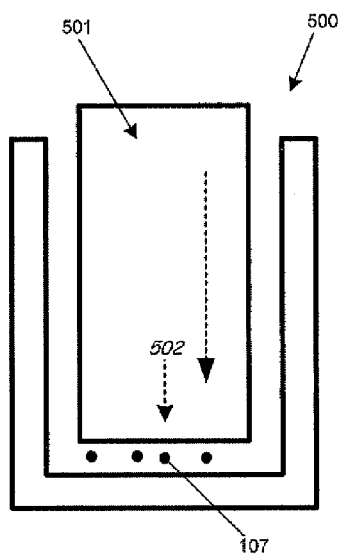
FIG. 6 is a schematic drawing showing methods improved upon by embodiments of the present invention.
Figure 7B:
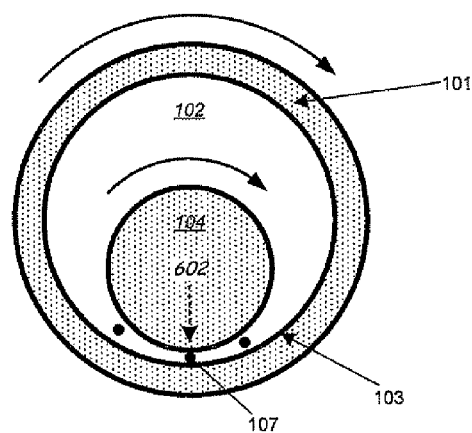
FIG. 7B is a schematic drawing showing methods according to an embodiment of the present invention.
Figure 7C:
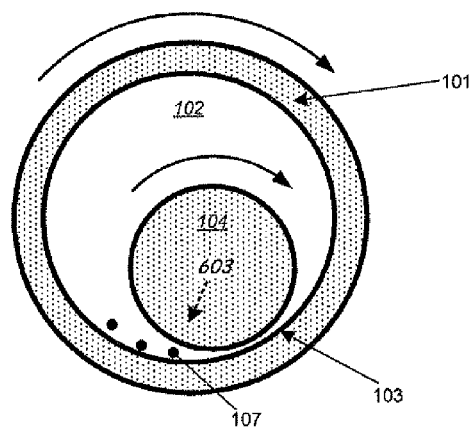
FIG. 7C is a schematic drawing showing methods according to an embodiment of the present invention.

Once the test sample 483 and a preselected volume of liquid of have been enclosed 454 in the testing cell 102 having a loose cylindrical rod 104 positioned therein 454, simulating downhole tool interactions upon the test sample can further include rotating 455 the cylindrical testing cell 102 containing the loose cylindrical rod 104 such that the loose cylindrical rod 104 rolls in relation to the cylindrical inner wall 103 of the testing cell 102 as can be shown with respect to FIG. 7A, FIG. 7B, and FIG. 7C. When the loose cylindrical rod 104 rolls in relation to the bottom portion of the cylindrical inner wall 103 of the testing cell, the loose cylindrical rod 104 applies a force to the plurality of bridging materials in the test sample 483, i.e., a crushing force between the loose cylindrical rod 104 and the cylindrical inner wall 103 of the testing cell 102, such that the test sample is partially crushed. The partially crushed test sample thus defines a resulting sample 484. The forces applied to the test sample 483 between the freely loose cylindrical rod 104 and the inner wall of the testing cell 102 are able to simulate downhole tool interactions upon the test sample 483, specifically the wet grinding action. A freely rolling loose cylindrical rod 104 that can roll along the bottom portion of the cylindrical inner wall 103 of a cylindrical testing cell 102 provides an enhanced simulation of downhole tool interactions over other types of actions, for example known methods for completely crushing particles, such the crushing action provided by a piston 501, for example, in apparatus 500 as can be shown with respect to FIG. 6. As can further be shown with reference to FIG. 5, the piston 501 is capable of subjecting the particles 107 only to a linear crushing force in only one direction 502. Furthermore, the piston 501 is capable of applying a force that is spread across all of the particles 107 at once.

As can be shown with reference to FIGS. 7A, 7B, and 7C, the freely rolling loose cylindrical rod rolls freely with respect to the inner surface 103 of the testing cell 102, thereby changing positions with respect to the particles 107 and haphazardly subjecting the particles 107 to forces in multiple directions, for example, directions 601, 602, and 603. Furthermore, the rolling action of the freely rolling loose cylindrical rod can alter the orientation of the particles 107 so that the particles 107 are subject to forces in more than one direction. Because the rolling action of the freely rolling loose cylindrical rod does not have to overcome the resistance of all particles 107 at once, less force can be applied to the particles 107 and the ability to achieve a partial crushing can be enhanced. The ability of the loose cylindrical rod 104 to haphazardly exert forces upon the granular material 107 thereby enhances the simulation of downhole tool interactions upon the test sample 483. Specifically, the haphazard rolling the loose cylindrical rod 104 freely along the cylindrical inner wall 103 of the cylindrical test cell 102 allows a simulation of the wet grinding process of a borehole environment that causes partial disintegration and dispersion of the bridging materials.

The cylindrical testing cell 102 can be included in a tubular container 101 as illustrated in FIG. 2A, and the loose cylindrical rod 104 can be rolled along the cylindrical inner wall 103 of the testing cell 102 by rotating the tubular container 101 and the cylindrical testing cell 102, also as illustrated in FIG. 2A. When the loose cylindrical rod 104 is rolled in relation to the cylindrical inner wall 103 of the cylindrical testing cell 102, the loose cylindrical rod 104 can apply force to the test sample 483 in the cylindrical testing cell such that the test sample 483 is partially crushed. The action of rotating the tubular container 101 can be performed at a constant preselected rotation speed for a predetermined time period. For example, an effective simulation of the wet grinding action of a borehole environment can be achieved with a rotation speed of 25-35 revolutions per minute (rpm) over a time of 1-4 hours, with a 1 hour duration providing sufficiently discriminatory test results.

When the step of rolling 455 the loose cylindrical rod 105 is complete, the test sample 483 has been subjected to forces that simulate downhole tool interactions in a manner that causes partial crushing of the test sample 483, such as the disintegration and dispersion of particles in the test sample 483 to a subset of the bridging materials, rendering the test sample 483 into a partially-degraded resulting sample 484. As a result of the partial crushing of the sized bridging materials in the test sample 483, the resulting sample 484, for example, may contain sized bridging materials of the test sample 483 that have decomposed or disintegrated into smaller sized bridging materials. It is not the purpose, however, for the resulting sample 484 to completely disintegrate; the resulting sample 484 may also contain sized bridging materials that were not crushed and maintained their original shape. For example, the resulting sample 484 will contain some of the original sized bridging materials, i.e., 600+ micron bridging materials. The resulting sample can contain both the durable sized bridging materials that were not crushed and the left over of particles that have been crushed. Accordingly, rolling the loose cylindrical rod 104 along the cylindrical inner wall 103 of the testing cell 102 provides a superior simulation of downhole tool interactions in comparison to using a dedicated crushing apparatus, like a piston apparatus 500, or a grinding apparatus, such as a planetary grinder, which might completely, rather than partially, render granular materials placed therein into a finer particulate matter and would therefore not accurately simulate downhole tool interactions upon the bridging materials.

Embodiments of methods according to the present invention can also include rotating the cylindrical tubular container about the second major axis is performed at a preselected rotational speed, for a preselected time period, and while the cylindrical tubular container is maintained at a preselected temperature. The preselected rotational speed, the preselected time period, and the preselected temperature for the rotation can be selected, for example, to best simulate downhole conditions and downhole tool interactions and wet grinding actions. For example, a preselected rotation speed between 25 and 35 revolutions per minute (rpm), a preselected time period of at least one hour, and a preselected temperature in the range of 20-150 degrees Celsius are capable of sufficiently simulating downhole tool conditions and downhole tool interactions and wet grinding actions in a manner that can produce consistent and meaningful test results. The preselected rotational speed, the preselected time period, and the preselected temperature can be enforced or maintained by implementing the structure as described with respect to the temperature-controlled rolling chamber 153, the heating element 154, and the motor 351.

Embodiments of methods according to the present invention can also include sieving 456 the resulting sample 484 using a sieve or sieves of a range of preselected size 434 (which can be, for example, the same preselected size 432 as used in the first sieving step 450) to create a durable sample 485 having particles within the predefined range of sizes. Sieving the resulting sample also allows the durable sample to be separated from the formulation of the resulting sample in the preselected volume of liquid. Accordingly, properties of the durable sample, as solids, can be measured rather than measuring the fluid properties (rheological properties or viscosity properties) of the formulation. The durable sample 485 contains sized bridging materials, for example, the 600+ micron bridging materials, that did not disintegrate or decompose to a size smaller than the preselected size of the sieve 434 as a result of the simulated downhole tool interactions in the rolling step 455. Sieving 456 the resulting sample 484 can also include, for example, shaking the sieve and washing the resulting sample with running water to remove all particles smaller than the preselected size. Sieving 456 can also include, for example, pouring the contents of the testing cell 102 directly into the appropriate sieve, and washing the contents using running tap water to remove all particles that are smaller then the preselected size 434.

Embodiments of methods according to the present invention can also include drying 457 the durable sample 485 at a high temperature to define a dry durable sample 486. As will be appreciate by those skilled in the art, the drying operation can be performed by any drying apparatus known to those of skill in the art, including, for example, an oven or micro-oven having a temperature controller and being capable of maintaining a constant temperature during the operation of drying the bridging materials in the durable sample 485. The oven can be, for example, a 115 volt gravity convection drying oven, model "174-50", manufactured or provided by OFI Testing Equipment, Inc. of Houston, Tex. In certain embodiments of the present invention, the drying operation can be performed at preselected temperature for a preselected time, for example at 105 degrees Celsius for a period of four or more hours. As will be appreciated by those of skill in the art, the drying apparatus can have a temperature controller and a time controller to perform the drying operation at the preselected temperature and for the preselected time. The drying operation 457 can be performed to enhance the consistency of the test procedure, allowing the bridging materials in the dry durable sample 482 to be measured without residual moisture being present therein, including retained moisture from the wet grinding simulation. The duration of the drying operation 457 may be equal to or greater than that of the drying operation 452 so that retained moisture from the wet grinding operation 455 may be eliminated, for example, with the preselected time being 8 hours or greater. Those of skill in the art will appreciate that the duration of the drying operation 457 and the duration of the drying operation 452 can be coordinated so that a consistent standard moisture level can be attained for the dry uniform batch 482 and the dry durable sample 486 to thereby enhance the accuracy of the testing procedure and the determined durability metric 488.

Embodiments of methods according to the present invention can also include measuring 458 a mass of the dry durable sample 486 to determine a durable mass 487. The mass of the dry durable sample 486 can be measured using techniques known in the art, such as using a balance or a digital balance, for example.

Embodiments of methods according to the present invention can also include 459 comparing the durable mass 487 to the initial mass 433 so that a durability metric 488 can be determined, the durability metric 488 being a quantification of the structural durability of the bridging materials in the test sample 483, and by extension, a quantification of the structural durability of the bridging materials in the bulk of bridging materials 431. Comparing the durable mass 487 to the initial mass 433 can include calculating a percentage loss of bridging materials, determining a coefficient of variation, and calculating the durability metric 488, which can be termed a "Bridging Material Stability Index" or "BMSI," as the ratio of the durable mass 487 to the initial mass 433.

Figure 8A:
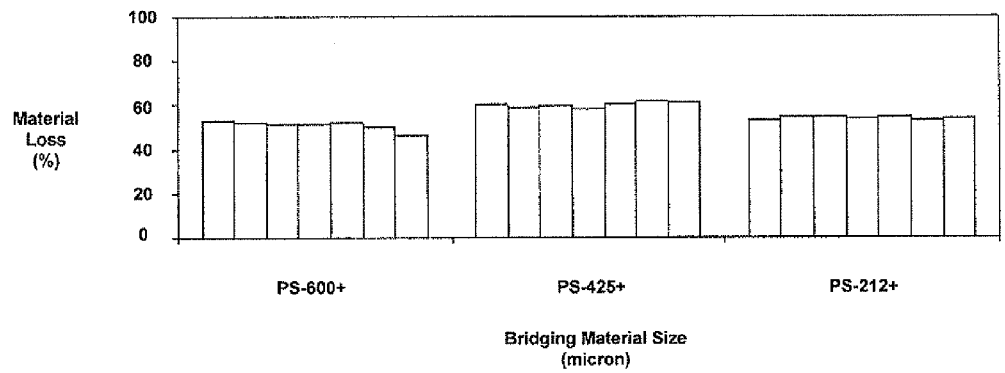
FIG. 8A is a chart showing data produced by embodiment of the present invention, the chart having percentage material loss on the Y-axis and bridging material size on the X-axis.
Figure 8B:
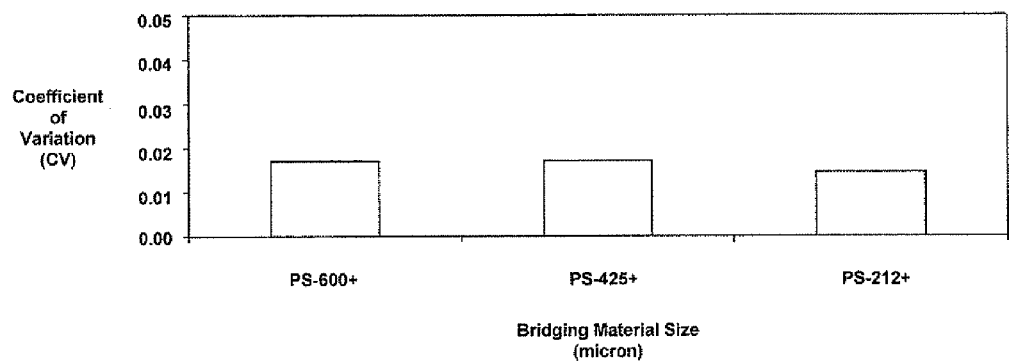
FIG. 8B is a chart showing data produced by embodiment of the present invention, the chart having coefficient of variation on the Y-axis and bridging material size on the X-axis.

Embodiments of methods according to the present invention can also include repeating multiple iterations of steps 451-459, for example, using multiple cut-point sizes as necessary for quality control and quality assurance of bridging materials. Each dry sample of the plurality of dry samples can be used, for example, in a separate iteration of the steps 453-459, to define an iteration of the test steps. A number of iterations in the range of 6-7 can provide a statistically significant test, provided that the results are averaged for each cut-point size. As can be shown with reference to FIG. 8A, embodiments of methods according to the present invention produce negligible variation in repeated test results for the same cut-point size of a given bulk of bridging materials, thereby providing a valid, reliable, and suitable method for quality control and quality assurance of different types of sized bridging materials. As can be shown with reference to FIG. 8B, the least-square coefficient of variation (CV) of the test results for three different sizes of the same bridging material suggests that the average percentage loss (%) of the bridging material represents a characteristics of the bridging material (i.e., the structural durability) and thus it can be used as a reliable test parameter for quality control and quality assurance of bridging materials used in the formulation of drill-in fluids.

Figure 8C:
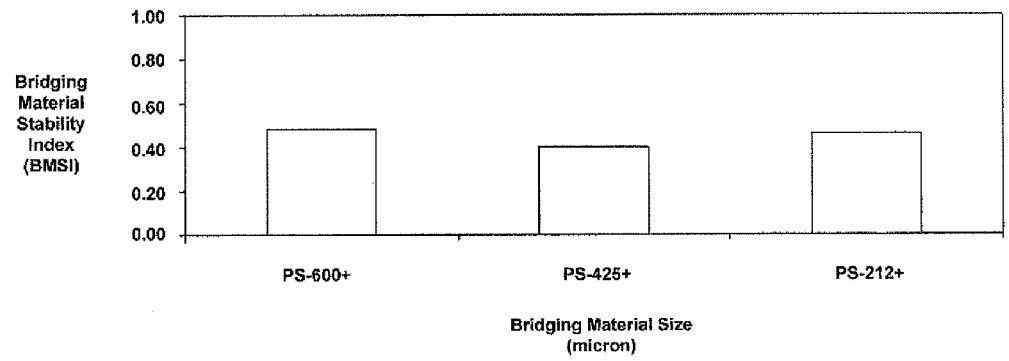
FIG. 8C is a chart showing data produced by embodiment of the present invention, the chart having a bridging material stability index on the Y-axis and bridging material size on the X-axis.

As can be shown with reference to FIG. 8C, an index parameter BMSI can be used to describe the relative structural durability of bridging materials in down hole conditions. The BMSI is defined as the ratio of the dry mass of the sized particles or bridging materials after the wet grinding process to the original dry mass of the cut point size that was used in the test. The analysis of BMSI shown in FIG. 7C indicate that more than 50% of the sized particles have been disintegrated to smaller sizes and thus passed away through the sieve. Hence, the bridging material tested has a stability index of less than 0.5. The technical significance of BMSI is that the disintegration of more than 50% of the original particles would effect a dramatic change in the particle size distribution of the bridging material in the mud during real-world downhole operation. Hence, the likelihood and impact of reservoir damage due to poor cake formation and particle migration is high.

The foregoing has broadly outlined certain objectives, features, and technical advantages of the present invention and a detailed description of the invention so that embodiments of the invention may be better understood in light of features and advantages of the invention as described herein, which form the subject of certain claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages is better understood from the following description when considered in connection with the accompanying figures. It is to be expressly understood, however, that such description and figures are provided for the purpose of illustration and description only and are not intended as a definition of the limits of the present invention.

That claimed is:

1. A method for testing and quantifying structural durability characteristics of sized bridging materials, the method comprising the following steps:
   sieving a bulk of the sized bridging materials to create a plurality of uniform batches, each uniform batch having particles within a predefined range;
   selecting a primary uniform batch and drying the primary uniform batch to remove residual moisture in the primary uniform batch to create a dry uniform batch;
   separating the dry uniform batch into a plurality of dry samples;
   selecting a dry sample from the plurality of dry samples to define a test sample, the test sample having an initial mass;
   sealing the test sample, a preselected volume of liquid, and a loose cylindrical rod in a cylindrical testing cell, the cylindrical testing cell having a substantially cylindrical inner wall;
   rotating the cylindrical testing cell containing the loose cylindrical rod such that the loose cylindrical rod rolls in relation to the cylindrical inner wall of the cylindrical testing cell, the loose cylindrical rod applying force to the test sample such that the test sample is partially crushed into a resulting sample, the resulting sample being partially suspended in the preselected volume of liquid;
   sieving the resulting sample to create a durable sample having particles within the predefined range that were not crushed by the force applied to the test sample, the durable sample thereby being separated from the preselected volume of liquid;
   drying the durable sample to remove residual moisture in the durable sample to create a dry durable sample;
   measuring the mass of the dry durable sample to define a durable mass; and
   comparing the durable mass to the initial mass to define a stability index.

2. A method as defined in claim 1, wherein:
   the predefined range of the particles is at or below 1000 microns;
   sieving the bulk of the sized bridging materials includes using a sieve having pores of a preselected size defining the largest particle size within the predefined range; and
   sieving the resulting sample includes using the sieve having pores of the largest particle size within the predefined range.

3. A method as defined in claim 2, wherein:
   the preselected size is 600 micron; and
   the initial mass is 25 grams.

4. A method as defined in claim 1, wherein the step of sealing the test sample, a preselected volume of liquid, and a loose cylindrical rod in a cylindrical testing cell includes the steps:
   inserting the loose cylindrical rod into the cylindrical testing cell before inserting the test sample into the cylindrical testing cell so as to reduce the risk that bridging materials in the test sample are crushed before performing the rotating step;
   inserting the preselected volume of liquid into the cylindrical testing cell;
   inserting the test sample into the cylindrical testing cell;
   sealing the testing cell using a removable sealing lid; and
   orienting the cylindrical testing cell so that a major axis of the loose cylindrical rod is substantially parallel to a major axis of the cylindrical testing cell.

5. A method as defined in claim 1 wherein:
the preselected volume of liquid is 350 ml; and
the preselected volume of liquid includes a liquid selected from the following liquids: tap water, sea water, salt water, simulated pore fluid, diesel, mineral oil, synthetic oil, esterified oil, or vegetable oil.

6. A method as defined in claim 1 wherein:
the preselected volume of liquid does not include chemical additives to chemically react with the test sample;
the step of comparing the durable mass to the initial mass does not include comparing resulting rheological properties of the resulting sample being partially suspended in the preselected volume of liquid to initial rheological properties of the test sample being partially suspended in the preselected volume of liquid; and
the step of comparing the durable mass to the initial mass does not include comparing resulting viscosity properties of the resulting sample being partially suspended in the preselected volume of liquid to initial viscosity properties of the test sample being partially suspended in the preselected volume of liquid.

7. A method as defined in claim 1, wherein:
the loose cylindrical rod is a cylinder having a mass of 600 grams or more; and
the cylindrical testing cell has a volume of 400 cubic centimeters or more.

8. A method as defined in claim 1, wherein:
the cylindrical testing cell is an interior compartment in a cylindrical tubular container, a first major axis of the cylindrical testing cell being substantially parallel with a second major axis of the cylindrical tubular container; and
the step of rotating the cylindrical testing cell containing the loose cylindrical rod such that the loose cylindrical rod rolls in relation to the cylindrical inner wall of the cylindrical testing cell includes the step of rotating the cylindrical tubular container about the second major axis.

9. A method as defined in claim 8, wherein the step of rotating the cylindrical tubular container about the second major axis is performed at a preselected rotational speed, for a preselected time period, and while the cylindrical tubular container is maintained at a preselected temperature, the preselected rotational speed, preselected time period, and preselected temperature being selected to simulate downhole tool interactions and wet grinding actions.

10. A method as defined in claim 8, wherein the preselected rotational speed is 35 revolutions per minute (rpm), the preselected time period is one hour, and the preselected temperature is selected from a range of 20-150 degrees Celsius.

11. A method as defined in claim 1, wherein:
the step of drying the primary uniform batch is performed for a first preselected time period and at a first preselected temperature;
the step of drying the durable sample is performed for a second preselected time period and at a second preselected temperature; and
the first preselected time period, the first preselected temperature, the second preselected time period, and the second preselected temperature are selected to allow a substantially uniform level of residual moisture in the dry uniform batch and the dry durable sample.

12. A method as defined in claim 1, wherein:
the first preselected time and the second preselected time are 4 hours; and
the first preselected temperature and the second preselected temperature are 105 degrees Celsius.

13. A method as defined in claim 1, wherein:
drying the primary uniform batch is performed while the uniform batch is in a sieve;
drying the durable sample is performed while the durable sample is in a sieve;
selecting the test sample is performed by measuring a mass of the test sample while the test sample is in the sieve and subtracting an empty mass of the sieve to determine the initial mass; and
measuring the mass of the dry durable sample is performed by measuring the mass of the dry durable sample while the dry durable sample is in the sieve and subtracting the empty mass of the sieve.

14. A method as defined in claim 1, the step of comparing the durable mass to the initial mass including the step of calculating a bridging material stability index (BMSI) based on a ratio of the durable mass to the initial mass, the BMSI quantifying the durability of the bridging materials when subjected to downhole tool interactions and wet grinding action.

15. An apparatus for testing the structural durability characteristics of bridging materials by simulating downhole tool interactions and wet grinding actions of a borehole environment upon the bridging materials, the apparatus comprising:
an elongated tubular container defining a testing container, the testing container having a cylindrical inner space therein bounded by a cylindrical inner wall of the testing container, a sealing cap to form a closed end of the testing container, and a sealing lid to close an open end of the testing container, the inner space defining a cylindrical testing cell, the cylindrical inner wall of the testing container defining a cylindrical inner wall of the cylindrical testing cell, the sealing lid being removable to allow physical access to the testing cell through the open end of the testing container so that bridging materials and a liquid may be positioned therein;
an elongated cylindrical rod positioned within the testing cell, the elongated cylindrical rod being positioned so that a major axis of the elongated rod is substantially parallel with a major axis of the testing container, the elongated cylindrical rod being able to roll freely along a bottom portion of the cylindrical inner wall of the cylindrical testing cell when the testing container is positioned horizontally and rotated, the elongated cylindrical rod defining a loose cylindrical rod, the loose cylindrical rod being able to simulate downhole tool interactions and wet grinding actions upon the bridging materials positioned within the testing cell by way of forces applied by the loose cylindrical rod while rolling freely along the bottom portion of the cylindrical inner wall of the testing cell when the testing cell is rotated; and
a roller in constant physical contact with a cylindrical outer wall of the testing container and positioned to apply a constant force to the cylindrical outer wall of the testing container so that the testing container rotates responsive to the constant force and the loose cylindrical rod positioned within the testing cell rolls freely along the bottom portion of the cylindrical inner wall of the testing cell to simulate downhole tool interactions and wet grinding actions upon the bridging materials positioned within the testing cell.

16. An apparatus as defined in claim 15, wherein the apparatus is bench-sized and the cylindrical testing cell and the loose cylindrical rod have dimensions selected to simulate downhole tool interactions and wet grinding actions of a borehole environment upon the bridging materials when the cylindrical testing cell is rotated and the loose cylindrical rod rolls freely across the bridging materials, the dimensions of the testing cell including a volume of at least 400 cubic centimeters (cc), a mass in a range of 3,200-3,300 grams, a length in a range of 7-8 inches, and an inner diameter in a range of 2-3 inches, the dimensions of the free rod including a mass in a range of 575-600 grams, a length in a range of 5.75-6.00 inches, and an outer diameter in a range of 1.25 to 1.75 inches.

17. An apparatus as defined in claim 15, wherein the sealing lid includes a relief valve to allow high temperature and high pressure within the testing cell and the sealing lid is securely attached to the open end of the testing container so that bridging materials, a preselected volume of liquid, and the loose cylindrical rod positioned within the cylindrical testing cell cannot escape the cylindrical testing cell.

18. An apparatus as defined in claim 15, the apparatus further comprising a motor to drive the rotation of the roller, the motor having a speed controller and a time controller so that the roller and the testing container rotate at a constant predetermined rotation rate for a predetermined time period to simulate downhole tool interactions and wet grinding actions upon the bridging materials positioned within the testing cell.

19. An apparatus as defined in claim 18, wherein:
the predetermined rotation rate is at least 25 revolutions per minute (rpm) and the predetermined time period is in a range of 1-4 hours to simulate downhole tool interactions and wet grinding actions; and
the time controller has a digital interface allowing a user to input a predetermined time period in one-minute increments.

20. An apparatus as defined in claim 15, wherein the roller and the elongated tubular container are enclosed in an insulated rolling cell, the insulated rolling cell including a temperature controller so that the cylindrical testing cell can be heated to a predetermined temperature.

21. An apparatus as defined in claim 20, wherein the predetermined temperature is in the range of 20 to 150 degrees Celsius to simulate downhole tool interactions and wet grinding actions.

22. An apparatus as defined in claim 15, wherein the bridging materials are defined as a test sample and wherein the test sample having been subjected to simulated downhole tool interactions and wet grinding actions is defined as a resulting sample, the apparatus further comprising:
one or more sieves for sieving a bulk of sized bridging materials to create a test sample having particles within a predefined range and for sieving a resulting sample to create a durable sample, the durable sample having particles within the predefined range; and
an oven for drying the test sample to remove residual moisture in the test sample and for drying the durable sample to remove residual moisture in the durable sample such that a mass of the test sample and a mass of the durable sample can be measured while the test sample and the durable sample each have a substantially uniform level of residual moisture.

23. A method for testing and quantifying structural durability characteristics of sized bridging materials, the method comprising the following steps:
sieving a bulk of the sized bridging materials to create a uniform sample having particles within a predefined range;
drying the uniform sample to remove residual moisture in the uniform sample to create a test sample, the test sample having an initial mass;
sealing the test sample, a preselected volume of liquid, and a loose cylindrical rod in a cylindrical testing cell, the cylindrical testing cell having a substantially cylindrical inner wall;
rotating the cylindrical testing cell containing the loose cylindrical rod such that the loose cylindrical rod rolls in relation to the cylindrical inner wall of the cylindrical testing cell, the loose cylindrical rod applying force to the test sample such that the test sample is partially crushed into a resulting sample, the resulting sample being partially suspended in the preselected volume of liquid;
sieving the resulting sample to create a durable sample having particles within the predefined range that were not crushed by the force applied to the test sample, the durable sample thereby being separated from the preselected volume of liquid;
drying the durable sample to remove residual moisture in the durable sample to create a dry durable sample;
measuring the mass of the dry durable sample to define a durable mass; and
comparing the durable mass to the initial mass to define a stability index.

24. A method as defined in claim 23, wherein:
the predefined range of the particles is at or below 1000 microns;
sieving the bulk of the sized bridging materials includes using a sieve having pores of a preselected size defining the largest particle size within the predefined range; and
sieving the resulting sample includes using the sieve having pores of the largest particle size within the predefined range.

25. A method as defined in claim 23, wherein:
the preselected size is 600 micron; and
the initial mass is 25 grams.

26. A method as defined in claim 23, wherein the step of sealing the test sample, a preselected volume of liquid, and a loose cylindrical rod in a cylindrical testing cell includes the steps:
inserting the loose cylindrical rod into the cylindrical testing cell before inserting the test sample into the cylindrical testing cell so as to reduce the risk that bridging materials in the test sample are crushed before performing the rotating step;
inserting the preselected volume of liquid into the cylindrical testing cell;
inserting the test sample into the cylindrical testing cell;
sealing the testing cell using a removable sealing lid; and
orienting the cylindrical testing cell so that a major axis of the loose cylindrical rod is substantially parallel to a major axis of the cylindrical testing cell.

27. A method as defined in claim 23 wherein:
the preselected volume of liquid is 350 ml; and
the preselected volume of liquid includes a liquid selected from the following liquids: tap water, sea water, salt water, simulated pore fluid, diesel, mineral oil, synthetic oil, esterified oil, or vegetable oil.

28. A method as defined in claim 23 wherein:
the preselected volume of liquid does not include chemical additives to chemically react with the test sample;
the step of comparing the durable mass to the initial mass does not include comparing resulting rheological properties of the resulting sample being partially suspended in the preselected volume of liquid to initial rheological properties of the test sample being partially suspended in the preselected volume of liquid; and the step of comparing the durable mass to the initial mass does not include comparing resulting viscosity properties of the resulting sample being partially suspended in the preselected volume of liquid to initial viscosity properties of the test sample being partially suspended in the preselected volume of liquid.

29. A method as defined in claim 23, wherein:
the loose cylindrical rod is a cylinder having a mass of 600 grams or more; and
the cylindrical testing cell has a volume of 400 cubic centimeters or more.

30. A method as defined in claim 23, wherein:
the cylindrical testing cell is an interior compartment in a cylindrical tubular container, a first major axis of the cylindrical testing cell being substantially parallel with a second major axis of the cylindrical tubular container; and
the step of rotating the cylindrical testing cell containing the loose cylindrical rod such that the loose cylindrical rod rolls in relation to the cylindrical inner wall of the cylindrical testing cell includes the step of rotating the cylindrical tubular container about the second major axis.

31. A method as defined in claim 30, wherein the step of rotating the cylindrical tubular container about the second major axis is performed at a preselected rotational speed, for a preselected time period, and while the cylindrical tubular container is maintained at a preselected temperature, the preselected rotational speed, preselected time period, and preselected temperature being selected to simulate downhole tool interactions and wet grinding actions.

32. A method as defined in claim 30, wherein the preselected rotational speed is 35 revolutions per minute (rpm), the preselected time period is one hour, and the preselected temperature is selected from a range of 20-150 degrees Celsius.

33. A method as defined in claim 23, wherein:
the step of drying the primary uniform batch is performed for a first preselected time period and at a first preselected temperature;
the step of drying the durable sample is performed for a second preselected time period and at a second preselected temperature; and
the first preselected time period, the first preselected temperature, the second preselected time period, and the second preselected temperature are selected to allow a substantially uniform level of residual moisture in the dry uniform batch and the dry durable sample.

34. A method as defined in claim 23, wherein:
the first preselected time and the second preselected time are 4 hours; and
the first preselected temperature and the second preselected temperature are 105 degrees Celsius.

35. A method as defined in claim 23, wherein:
drying the primary uniform batch is performed while the uniform batch is in a sieve;
drying the durable sample is performed while the durable sample is in a sieve;
selecting the test sample is performed by measuring a mass of the test sample while the test sample is in the sieve and subtracting an empty mass of the sieve to determine the initial mass; and
measuring the mass of the dry durable sample is performed by measuring the mass of the dry durable sample while the dry durable sample is in the sieve and subtracting the empty mass of the sieve.

36. A method as defined in claim 23, the step of comparing the durable mass to the initial mass including the step of calculating a bridging material stability index (BMSI) based on a ratio of the durable mass to the initial mass, the BMSI quantifying the durability of the bridging materials when subjected to downhole tool interactions and wet grinding action.

* * * * *